United States Patent [19]

Laali et al.

[11] Patent Number: 5,284,051

[45] Date of Patent: Feb. 8, 1994

[54] METHOD FOR IDENTIFYING RESIDUAL OIL CHARACTERISTICS OF POROUS RESERVOIR ROCK

[75] Inventors: Hooman Laali; Ralph Navarro, Jr., both of Dallas, Tex.

[73] Assignee: Mobil Oil Corporation, Fairfax, Va.

[21] Appl. No.: 15,014

[22] Filed: Feb. 9, 1993

[51] Int. Cl.[5] .............................................. E21B 49/00
[52] U.S. Cl. .......................................... 73/153; 73/38
[58] Field of Search ..................... 73/153, 38; 250/373, 250/255; 436/27, 31

[56] References Cited

U.S. PATENT DOCUMENTS

| | | | |
|---|---|---|---|
| 3,380,292 | 4/1968 | Fournier | 73/38 |
| 3,839,899 | 10/1974 | McMillen | 73/38 |
| 3,856,468 | 12/1974 | Keller | 436/27 |
| 4,291,271 | 9/1981 | Lauffer | 324/307 |
| 4,379,407 | 4/1983 | Masse et al. | 73/579 |
| 4,543,821 | 10/1985 | Davis, Jr. | 73/38 |
| 4,672,840 | 6/1987 | Cullick | 73/38 |
| 4,688,238 | 8/1987 | Sprunt et al. | 378/4 |
| 4,799,382 | 1/1989 | Sprunt et al. | 73/38 |
| 4,907,442 | 3/1990 | Jones et al. | 73/38 |
| 5,012,674 | 5/1991 | Millheim et al. | 73/153 |

FOREIGN PATENT DOCUMENTS 8502015  5/1985  United Kingdom ................ 250/255

Primary Examiner—Robert J. Warden
Assistant Examiner—Laura E. Collins
Attorney, Agent, or Firm—Alexander J. McKillop; George W. Hager, Jr.

[57] ABSTRACT

A first fluid having a dyed styrene monomer is injected into a porous reservoir rock to effect saturation. A second fluid, miscible with the first fluid and having a dyed styrene monomer differing in color from the first fluid, is injected into the porous rock to displace the first fluid. Effluent flow from the porous rock is monitored with UV-visible light spectroscopy for use in determining oil displacement characteristics of the porous rock. Subsequent rapid polymerization of the styrene monomer within the porous rock allows identification and characterization of the controlling factors and attributes of the pore network responsible for entrapment of the residual phase. This allows assessment of larger intervals of the reservoir rock.

4 Claims, 1 Drawing Sheet

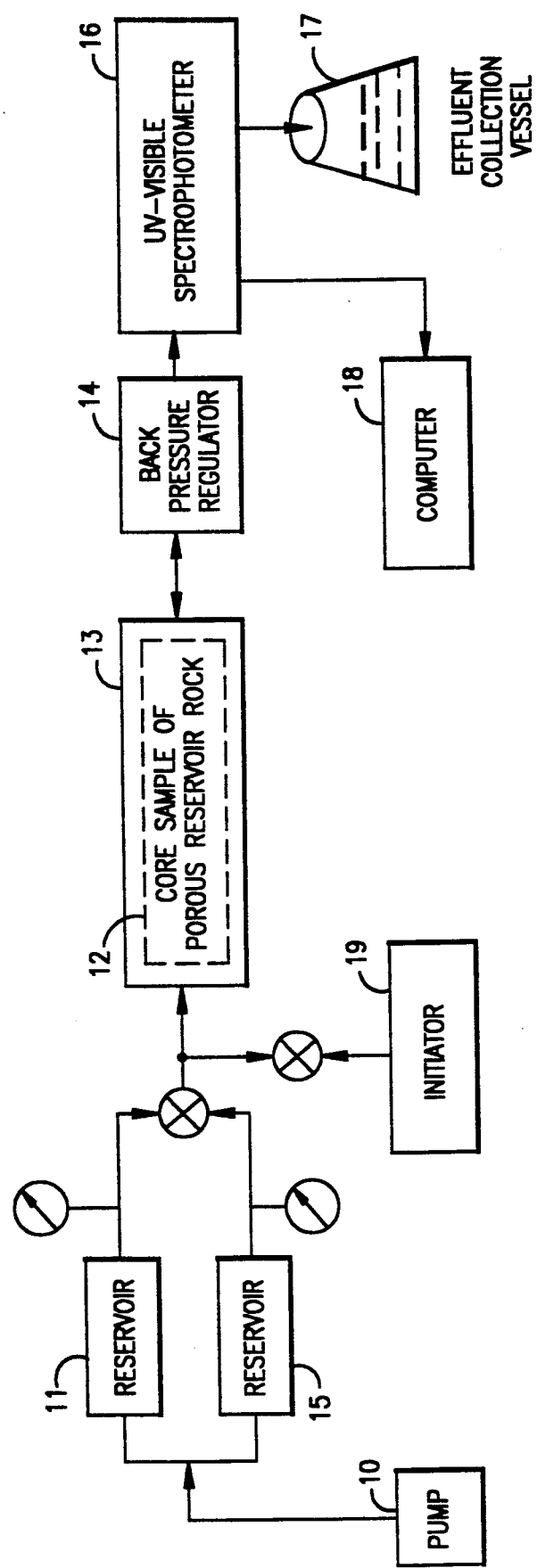

METHOD FOR IDENTIFYING RESIDUAL OIL CHARACTERISTICS OF POROUS RESERVOIR ROCK

BACKGROUND OF THE INVENTION

In the production of oil from subterranean reservoirs, it is usually possible to recover only a small fraction of the total oil present in the formation by so-called primary recovery methods which utilize only the natural forces present in the reservoir. To recover oil beyond that which is produced by primary methods, a variety of supplemental production techniques have been employed. In these supplementary techniques, commonly referred to as enhanced recovery operations, a fluid is introduced into the oil-bearing formation in order to displace oil to a production system comprising one or more production wells. The displacing or "drive" fluid may be an aqueous liquid such as brine or fresh water, a gas such as carbon dioxide, steam or dense-phase carbon dioxide, an oil-miscible liquid such as butane, or an oil and water-miscible liquid such as an alcohol.

In miscible flooding operations, it is important to be able to determine the efficiency with which oil can be displaced from porous reservoir rock. Previous attempts at identification and quantification of pore systems and their attributes that effect residual oil and recovery efficiency during miscible flooding have been unsatisfactory, particularly in carbonate reservoir rocks, due to extreme complexity and heterogeneity.

SUMMARY OF THE INVENTION

The present invention is directed to a method for determining the efficiency with which oil can be displaced from porous reservoir rock. More particularly, a porous reservoir rock is saturated with a first fluid including a first dyed styrene monomer. A second fluid which is miscible with the first fluid and includes a second dyed styrene monomer of a differing color from the first dyed styrene monomer is used to displace the first fluid from the porous rock. Effluent flow from the porous rock is monitored with UV-visible light spectroscopy. Effluent concentration is determined as a function of the volume of second fluid injected into the porous rock. Residual oil in the porous rock is quantified under miscible conditions by matching the effluent fluid flow profile to that of a capacitance-dispersion model.

After displacement flooding, the styrene monomer dyed differently for the displacing and displaced phases is subjected to rapid polymerization within the porous rock. Rapid polymerization and subsequent slabbing and thin-sectioning of the porous rock allows identification and characterization of pores that are responsible for entrapment of the residual phase.

BRIEF DESCRIPTION OF THE DRAWING

The sole drawing FIGURE illustrates apparatus useful for carrying out fluid displacement operations on a core sample of porous rock in accordance with the present invention.

DESCRIPTION OF THE PREFERRED EMBODIMENT

Referring to the drawing, a positive displacement pump 10 drives a first fluid having a blue-dyed styrene monomer from a reservoir 11 to fully saturate a core sample of a porous reservoir rock 12 contained in a suitable pressure vessel 13 that can be pressurized up to several thousand pounds per square inch. Typical of such pressure vessels are those described in U.S. Pat. Nos. 3,839,899 to McMillan; 4,688,238 to Sprunt et al; and 4,379,407 to Masse et al., the teachings of which are incorporated herein by reference. A second fluid having a red-dyed styrene monomer is then driven from reservoir 15 by pump 10 to displace the first fluid from the porous rock 12 at a low constant rate of about 1 to 3 $cm^3$/hr and against a back pressure of approximately 1200 psig at room temperature controlled by regulator 14. Both first and second fluids within reservoirs 11 and 15 are preferably the same fluid to allow for optimum (first contact) miscibility conditions within the porous rock 12 during fluid displacement. First contact miscibility eliminates fluid phase behavior problems such as gravity segregation and viscous instability and ensures that entrapment of oil within the porous rock is due solely to pore structure. Following displacement, the dye-labelled styrene monomer in the pores of the porous rock 12 is rapidly polymerized aided by the use of an initiator 19. In solution, the initiator decomposes on heating and provides free radicals which initiate the polymerization process. Fast rate of free radical formation results in rapid polymerization. An example is the use of the commercially available "VAZO" initiators manufactured by Dupont Company. Since decomposition is first-order, the rate of free radical formation can be controlled by regulating the temperature. The "VAZO" initiators are ideal for this procedure because they readily dissolve in styrene monomer and do not produce oxygenated residues so that they may be used with dyes without significant color degeneration. The amount used is usually 0.8% by weight. The amount used may vary from 0.01% or less to 1% or more depending on the desired reaction speed and expected brittleness and other variables. A 0.8% "VAZO 67" initiator concentration in a 250 milliliter styrene solution decomposes significantly when subjected to 100(C.) degrees resulting in polymerization in 15 to 20 minutes, depending on the amount of dyes in the solution. The initiator does not decompose at lower room temperature and therefore is stable in the solution of dyed styrene while being utilized as a flooding medium.

The effluent concentration is monitored with a UV-visible light spectrophotometer 16 and collected in an effluent collection vessel 17. Use of the two differing color dyed styrene monomers in the first and second miscible fluids with the aid of UV-visible light spectroscopy allows accurate monitoring of the effluent concentration as a function of the volume of the displacing second fluid by the computer 18. Both qualitative and quantitative applications of light spectroscopy is relied upon. The qualitative application of absorption spectrometry is based on the fact that the styrene monomer, blue dye, and the red dye each absorb light only in specific regions of the spectrum. The quantification application is based on the fact that when an electromagnetic wave of a specific wavelength travels through a dyed solution of styrene monomer, the fraction of the radiation absorbed is a function of the concentration of the dyed styrene monomer in the light path. The complications of reflection, scattering, and window absorption, and thickness of the solution is avoided through reference to a blank contained in the same sample curve.

The effluent concentration is determined according to the following:

i) A set of known standards are prepared from the dyed styrene displaced and displacing solutions. These standards are prepared very accurately and carefully and cover a wide range of concentrations from 0% to 100%.

ii) Using a light spectrophotometer, the absorbance of light at a specific wavelength sensitive to all mixtures of the blue and red-dyed styrene concentrations (685 nm) is measured and recorded for all known standards.

iii) The absorbance value is plotted against known concentrations to obtain a well-defined relationship between the dyed styrene solutions and absorbance at the given wavelength (685 nm). A second order polynomial regression (fits experimental data points accurately with a correlation factor of 0.999 to 1.00) is defined.

iv) During the course of displacement flooding of the core sample, the computer is programmed to repeatedly measure the absorbance of certain wavelength (685 nm) passing through the effluent as it moves through a flow cell cuvette in the light spectrophotometer. The absorbance is thus obtained and recorded against the injected volume of displacing solution. Concentration of the effluent is then calculated for each measurement from the regression formula already developed between absorbance and the known standards.

Quantification of residual oil within the porous rock is further determined by the computer 18 by the matching of the effluent profile to that based on a capacitance-dispersion model. Previous work by other investigators details quantification of the parameters that define flow and miscible flood residual oil saturation values by history matching the profile of effluent concentration vs. injected pore volume of the displacing fluid to the mathematical model of Coats and Smith. Spence, A.P. and Watkins, R.W.: The effect of microscopic core heterogeneity on miscible flood residual oil saturation: Paper SPE 9229 presented at 55th Annual Fall Technical Conference and Exhibition of the Society of Petroleum Engineers, Dallas, Tex., Sep. 21-24, 1980; and Bretz, R.E., Specter, R.M., and Orr, F.M.: Effect of pore structure on miscible displacements in laboratory cores: Paper SPE 15017 presented at Permian Basin Oil and Gas Recovery Conference of the Society of Petroleum Engineers, Dallas, Tex., Mar. 13-14, 1986. For this procedure, an equivalent miscible flood residual oil value is calculated from a material balance as explained below:

i) The pore volume of the core plug is determined accurately after it is cleaned and dried as part of routine plug analysis.

ii) After displacement flooding, the concentration of the displaced fluid in the effluent as function of injected displacing volume is calculated as a explained above.

iii) A material balance is conducted. The sum of the volume of the displaced phase from the start of displacing phase injection (0% displacing phase concentration in the effluent) to the point representing the first reading of 100% displacing phase concentration in the effluent is obtained (concentration x volume fraction for each increment). Since the core plug was initially 100% saturated with the displaced phase prior to injection of the displacing phase, the amount of the volume equivalent to the difference between pore volume of the core plug and the sum of produced displaced phase volume represents the equivalent residual oil saturation to miscible flooding (expressed as a percentage of the core pore volume).

iv) If displacement flooding is stopped prior to reaching the point representing the first reading of 100% displacing phase concentration in the effluent, the equivalent residual oil to miscible flooding may be calculated from a regression equation based on the available data points (effluent concentration vs. pore volume injected). Such a regression equation is further useful for determining oil saturations as a function of pore volume of injected displacing miscible fluid for that particular reservoir rock type. This is more typical of the actual field-scale flooding where usually solvent volumes representing only a fraction of the reservoir's pore volume is injected.

Such quantification allows assessment of the unit displacement efficiency for each reservoir rock type.

The rapid polymerization of the dye-labelled styrene monomer in the pores of the porous rock 12 preserves the distribution of each phase within the porous rock and allows cutting and polishing of the core sample. The method of the present invention thus allows for identification of the controlling factors affecting entrapment of the residual oil phase and its association with some identifiable reservoir rock feature. Also, residual oil characterization of a larger reservoir interval may be carried out.

While a preferred embodiment of the present invention has been described, numerous modifications and alterations may be made without departing from the spirit and scope of the invention as set forth in the appended claims.

We claim:

1. Method for determining the efficiency with which oil can be displaced from porous reservoir rock, comprising the steps of:

a) fully saturating a porous reservoir rock with a first fluid including a first dyed styrene monomer, b) injecting a second fluid which is miscible with said first fluid and includes a second dyed styrene monomer of a differing color dye from said first dyed styrene monomer to displace said first fluid from said porous rock, and c) monitoring effluent flow of said first and second fluids from said porous rock with UV visible light spectroscopy for identifying an oil displacement characteristic of said porous rock.

2. The method of claim 1 further comprising the step of injecting an initiator into said porous rock which decomposes and provides free radicals which initiate polymerization of styrene monomer remaining in said porous rock.

3. The method of claim 1 wherein the step of monitoring effluent flow from said porous rock includes the step of determining the concentration of said first fluid in the effluent flow as a function of volume of said second fluid injected into a core sample.

4. The method of claim 3 further comprising the step of quantifying residual oil in said porous rock under miscible conditions by determining the difference between pore volume of the core sample and volume of the displaced first fluid.

* * * * *